US010612010B2

(12) United States Patent
Lee et al.

(10) Patent No.: US 10,612,010 B2
(45) Date of Patent: Apr. 7, 2020

(54) THERMOPHILE-DERIVED KERATINASE AND USE THEREOF

(71) Applicant: KYUNGPOOK NATIONAL UNIVERSITY INDUSTRY-ACADEMIC COOPERATION FOUNDATION, Daegu (KR)

(72) Inventors: Dong Woo Lee, Daegu (KR); Yong Jik Lee, Daegu (KR); Hyun Su Jin, Daegu (KR); Ji Yeon Kim, Daegu (KR); Gae Won Nam, Cheongju (KR); Sang Jae Lee, Busan (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 210 days.

(21) Appl. No.: 15/509,095

(22) PCT Filed: Sep. 7, 2015

(86) PCT No.: PCT/KR2015/009419
§ 371 (c)(1),
(2) Date: Mar. 6, 2017

(87) PCT Pub. No.: WO2016/036222
PCT Pub. Date: Mar. 10, 2016

(65) Prior Publication Data
US 2017/0355971 A1 Dec. 14, 2017

(30) Foreign Application Priority Data
Sep. 5, 2014 (KR) .................... 10-2014-0118995

(51) Int. Cl.
*C12N 9/00* (2006.01)
*C12N 15/52* (2006.01)
*C12N 9/48* (2006.01)
*C12N 9/10* (2006.01)
*C12N 9/02* (2006.01)

(52) U.S. Cl.
CPC ............... *C12N 9/13* (2013.01); *C12N 9/00* (2013.01); *C12N 9/0051* (2013.01); *C12N 9/48* (2013.01); *C12N 9/485* (2013.01); *C12N 15/52* (2013.01); *C12Y 108/01009* (2013.01); *C12Y 208/01007* (2013.01); *C12Y 304/16005* (2013.01)

(58) Field of Classification Search
CPC .......................................................... A61K 8/65
See application file for complete search history.

(56) References Cited

U.S. PATENT DOCUMENTS 5,569,599 A  10/1996  Antranikian

OTHER PUBLICATIONS

Zhang et al., "Function of the in vitro Recombinant SufS—SufE Complex in the Fe—S Cluster Biosynthesis Pathway from the Thermus thermophilus", Chinese J. of Biochem. And Mol. Biol., Jun. 2014, 30(5):496-502.*
Lee et al. Genome sequence of a native-feather degrading extremely thermophilic Eubacterium, Fervidobacterium islandicum AW-1Standards in Genomic Sciences, 2015, 10:71, pp. 1-9. DOI 10.1186/s40793-015-0063-4.*
Frederich et al., "Keratin Degradation by Fervidobacterium pennavorans, a Novel Thermophilic Anaerobic Species of the Order Thermotogales", Applied and Environmental Microbiology, Aug. 1996, vol. 62, No. 8, p. 2875-2882.*
Lucas et al., "Complete sequence of Fervidobacterium pennivorans DSM 9078." Submitted (Mar. 2012) to the EMBL/GenBank/D—retrived from < https://www.uniprot.org/proteomes/UP000007384 > on Jun. 28, 2019.*
Yassin M. El-Ayouty, Amira El-Said, Ahmed M. Salama Purification and characterization of a keratinase from the feather-degrading cultures of Aspergillus flavipes African Journal of Biotechnology vol. 11(9), pp. 2313-2319, Jan. 31, 2012 ISSN 1684-5315 © 2012 Academic Journals.
Sri Rahayu, Dahrul Syah, Maggy Thenawidjaja Suhartono Degradation of keratin by keratinase and disulfide reductase from *Bacillus* sp. MTS of Indonesian origin Biocatalysis and Agricultural Biotechnology 1 (2012) 152-158.
S Rahayu, D Syah, MT Suhartono Preliminary Study on Keratinase from Two Indonesian Isolates S Rahayu et al/Animal Production 12 (1):60-68, 2012.
Gae-Won Nam, Dong-Woo Lee, Han-Seoong Lee, Nam-Ju Lee, Byoung-Chan Kim, Eun-Ah Choe, Jae-Kwan Hwang, Maggy T. Suhartono, Yu-Ryang Pyun Native-feather degradation by Fervidobacterium islandicum AW-1, a newly isolated keratinase-producing thermophilic anaerobe Arch Microbiol (2002) 178 :538-547.

(Continued)

*Primary Examiner* — Suzanne M Noakes
(74) *Attorney, Agent, or Firm* — Weisun Rao; Venture Partner, LLC

(57) ABSTRACT

The present invention relates to a novel thermophile-derived keratinase having keratin decomposition ability. Further, the present invention relates to a polynucleotide encoding the keratinase, a recombinant vector containing the same, host cells transformed by using the recombinant vector, and a method for preparing a keratinase including a step of culturing the host cells. Further, the present invention relates to a composition for decomposing keratin containing the enzyme; and a method for decomposing keratin by using the same. Further, the present invention relates to a keratin decomposed product decomposed by the enzyme.

The keratinase according to the present invention rapidly and effectively decomposes hardly-decomposable keratin, and thus it is expected that the keratinase can be used for the effective treatment and the high value-added resource recovery of agricultural and livestock waste, which causes environmental problems (for example, a novel material for enzyme cosmetics), and can be used in an innovative enzymatic bioconversion technique utilizing various decomposition enzyme groups.

7 Claims, 8 Drawing Sheets
Specification includes a Sequence Listing.

(56) References Cited

OTHER PUBLICATIONS

Alessandro Riffel, Adriano Brandelli, Cla'udia De M. Bellato, Gustavo H.M.F. Souza, Marcos N. Eberlin, Flavio C.A. Tavares Purification and characterization of a keratinolytic metalloprotease from *Chryseobacterium* sp. kr6 Journal of Biotechnology 128 (2007) 693-703.
BLAST ® Basic Local Alignment Search Tool NCBI/BLAST/ blastp suite/ Formatting Results 1BGJJB9F016 Oct. 8, 2015.
BLAST ® Basic Local Alignment Search Tool NCBI/ BLAST/ blastp suite/ Formatting Results 1BGPTZNJ01R Oct. 8, 2015.
BLAST ® Basic Local Alignment Search Tool NCBI/ BLAST/ blastp suite/ Formatting Results 1BGT19SH014 Oct. 8, 2015.
BLAST ® Basic Local Alignment Search Tool NCBI/ BLAST/ blastp suite/ Formatting Results 1BGWSZJB014 Oct. 8, 2015.

\* cited by examiner

[Fig. 1]
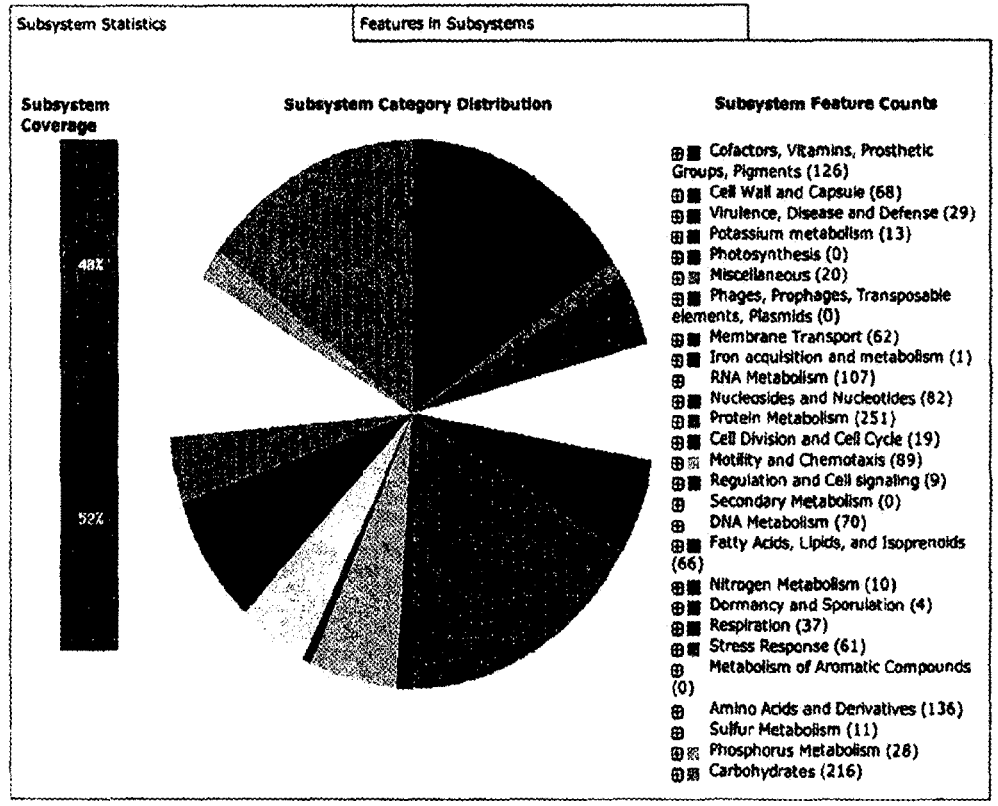

[Fig. 2]

| Function | Subsystem | F. islandicum AW-1 | F. pennivorans DSM 9078 | F. nodosum Rt17-B1 | T. maritima MSB8 |
|---|---|---|---|---|---|
| Cysteine desulfurase (EC 2.8.1.7), SufS subfamily | Alanine biosynthesis | + | + (84,92) | − | + (57,76) |

( , ) : Compare amino acid sequence with F. islandicum (identity%, similarity%).

[Fig. 3]

| Function | Subsystem | F. islandicum AW-1 | F. pennivorans DSM 9078 | F. nodosum Rt17-B1 | T. maritima MSB8 |
|---|---|---|---|---|---|
| Thermostable carboxypeptidase1 (EC 3.4.17.19) | Metallo-carboxypeptidases (EC 3.4.17.-) | + | + (85,95) | + (68,85) | − |

( , ) : Compare amino acid sequence with F. islandicum (identity%, similarity%).

[Fig. 4]

| Function | Subsystem | F. islandicum AW-1 | F. pennivorans DSM 9078 | F. nodosum Rt17-B1 | T. maritima MSB8 |
|---|---|---|---|---|---|
| Thioredoxin reductase (EC 1.8.1.9) | Thioredoxin-disulfide reductase, pyrimidine conversions | + | + (95,98) | + (91,96) | + (67,80) |

( , ) : Compare amino acid sequence with F. islandicum (identity%, similarity%).

[Fig. 5]

| Function | Subsystem | F. islandicum AW-1 | F. pennivorans DSM 9078 | F. nodosum Rt17-B1 | T. maritima MSB8 |
|---|---|---|---|---|---|
| Putative iron-sulfur cluster assembly scaffold protein for SUF system, SufE2 | Iron-sulfur cluster assembly | + | + (93,99) | − | + (53,71) |

( , ) : Compare amino acid sequence with F. islandicum (identity%, similarity%).

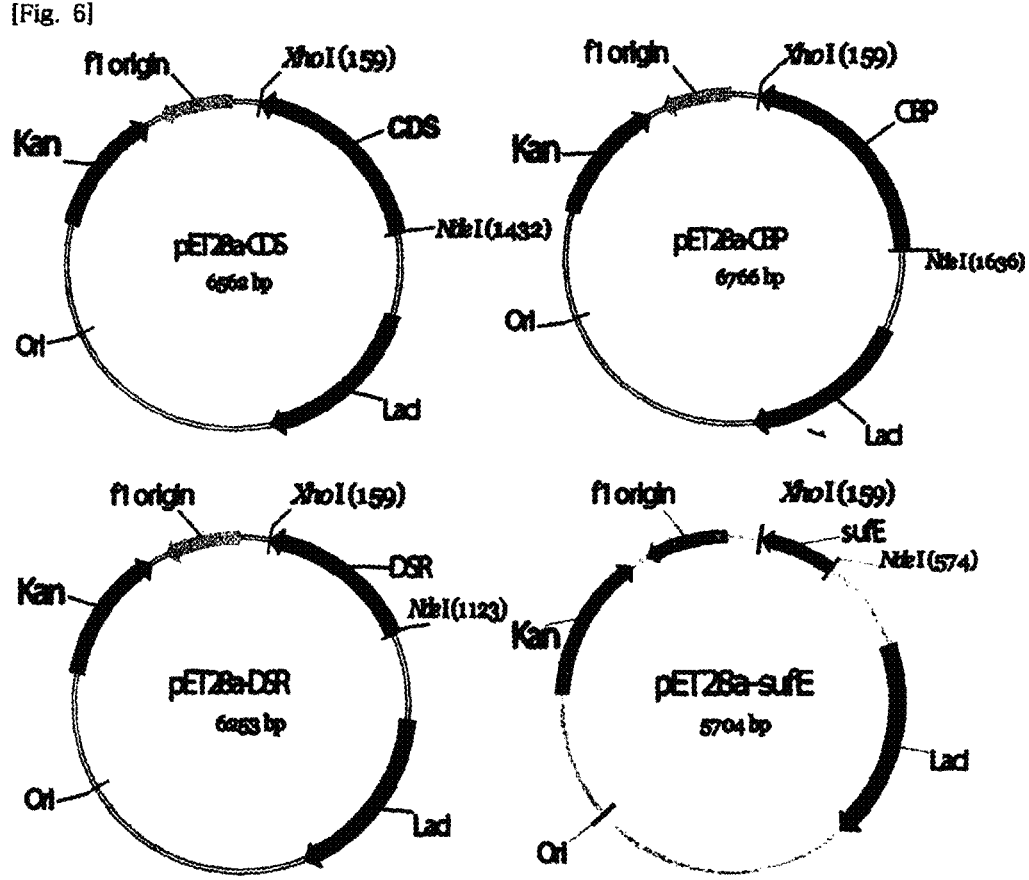
[Fig. 6]

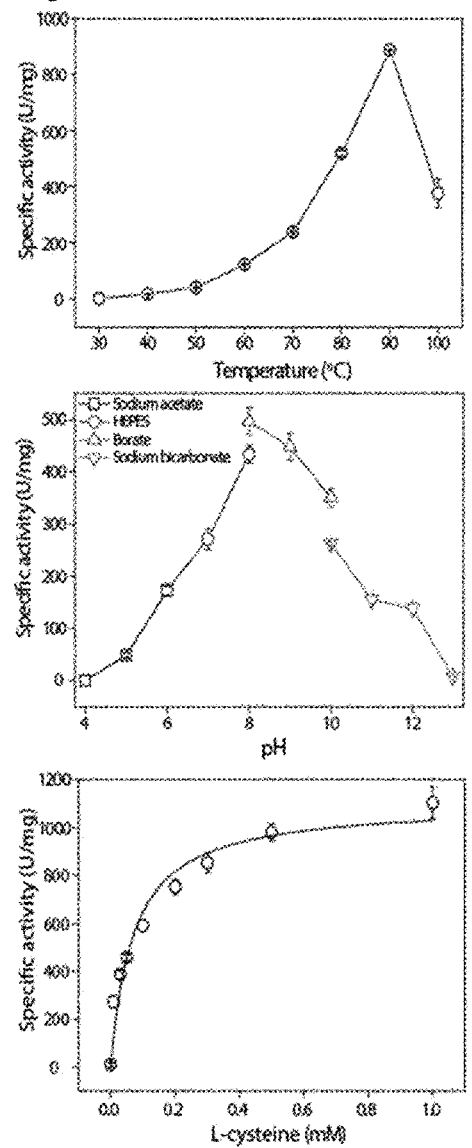
[Fig. 7]

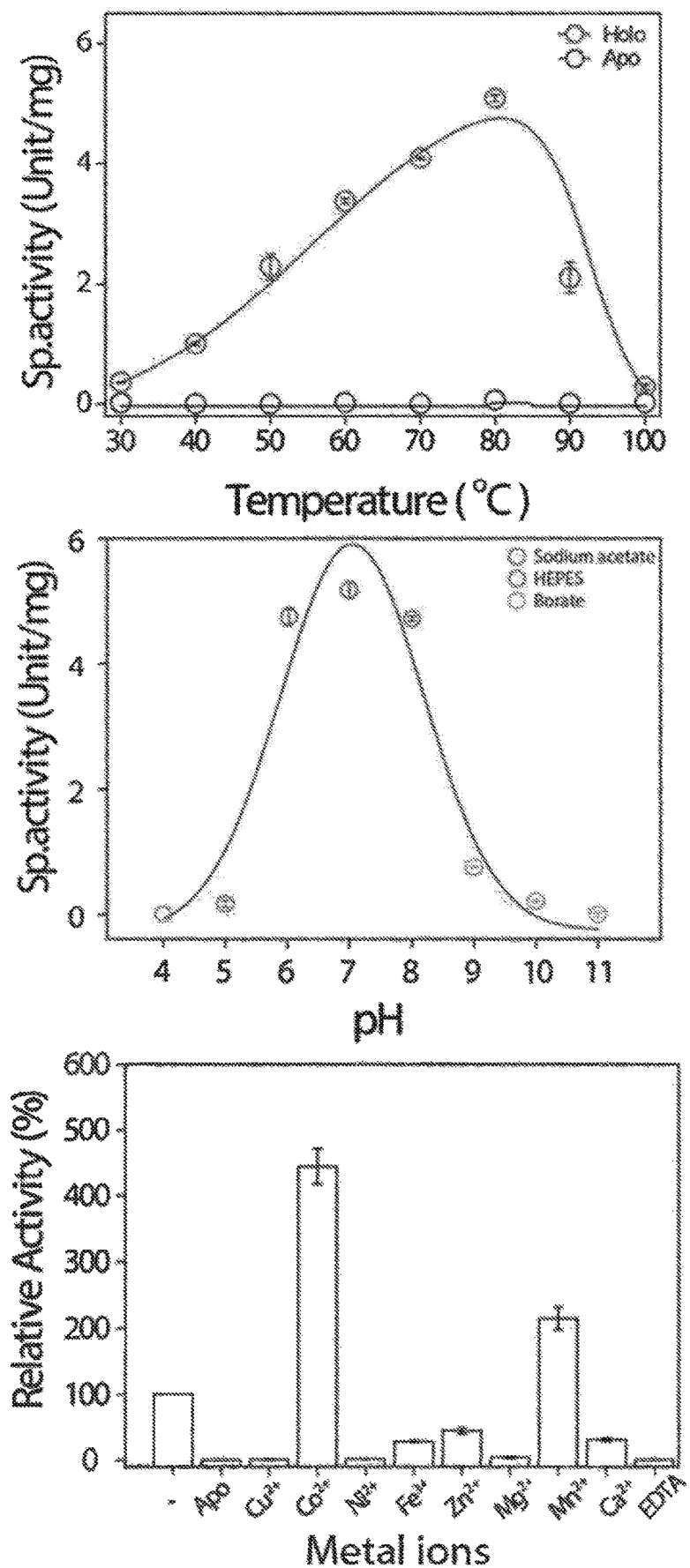
[Fig. 8]

[Fig. 9]
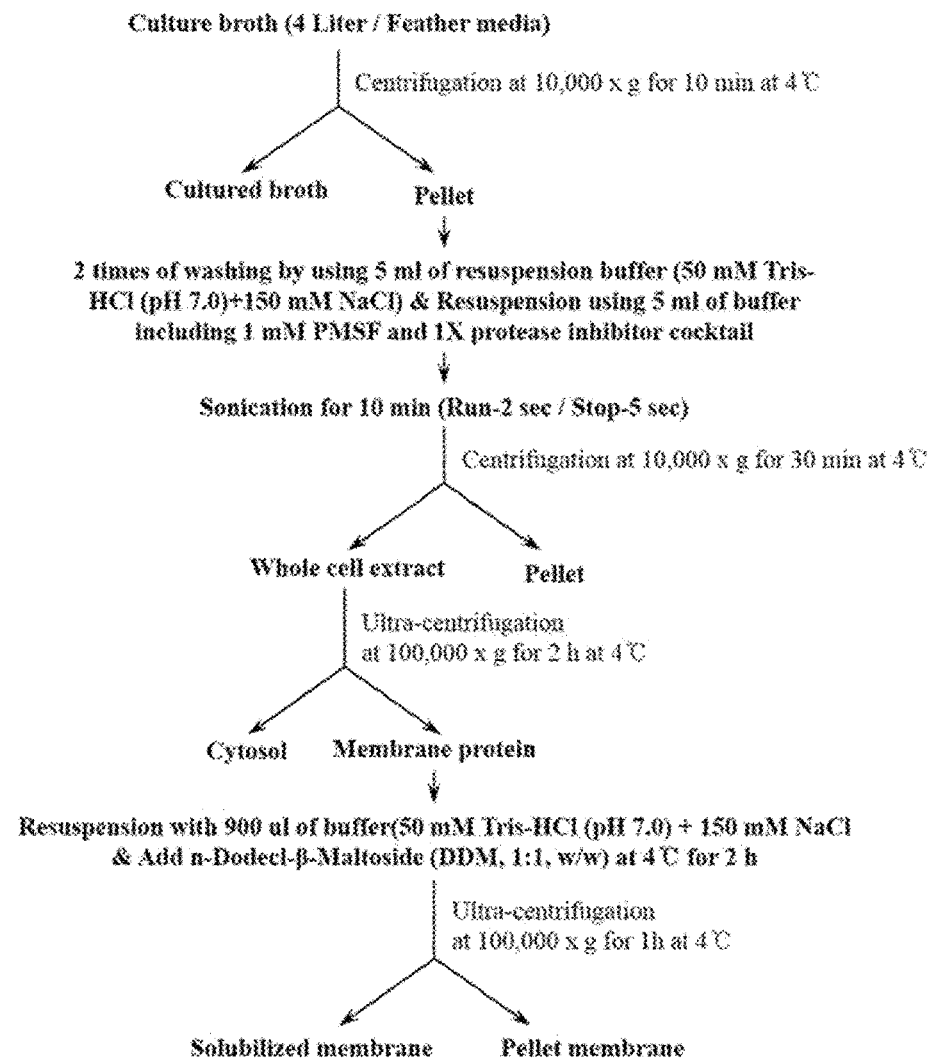
[Fig. 10]
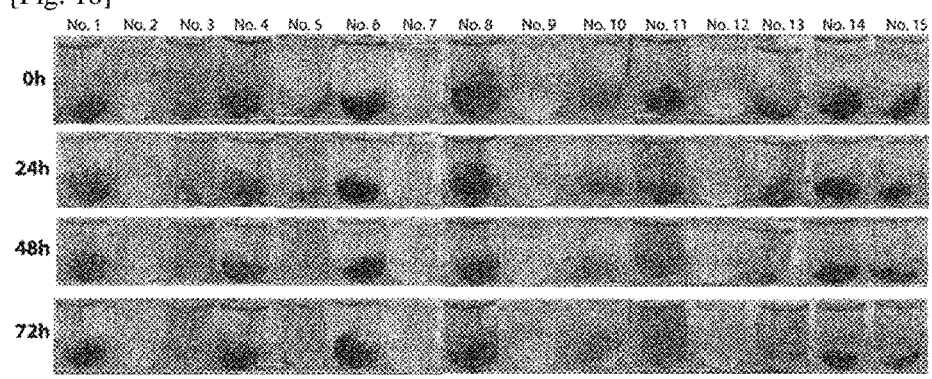

[Fig. 11]
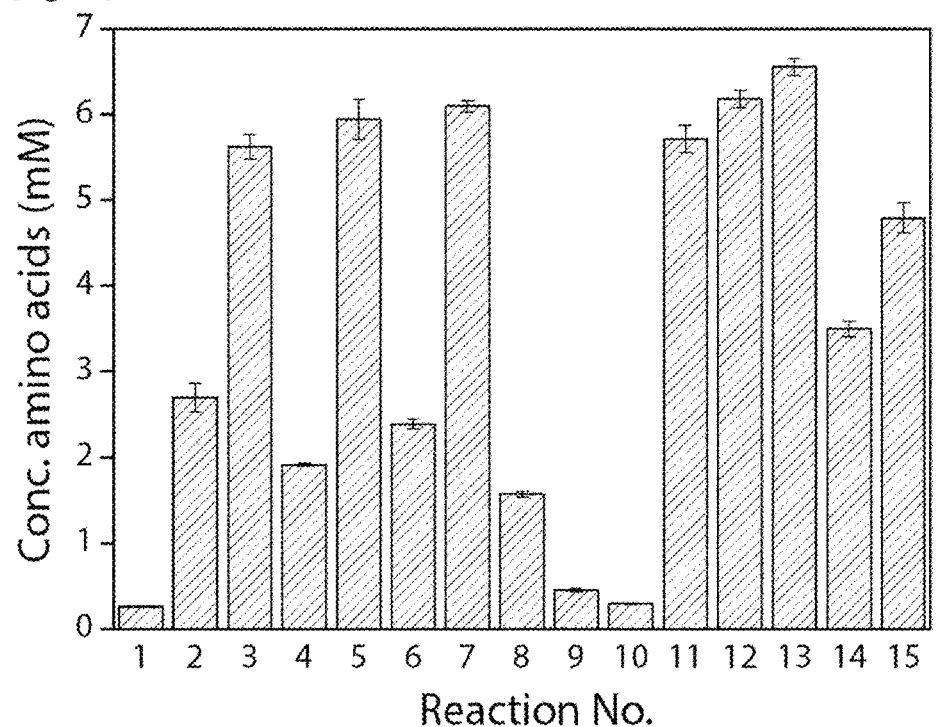
[Fig. 12]
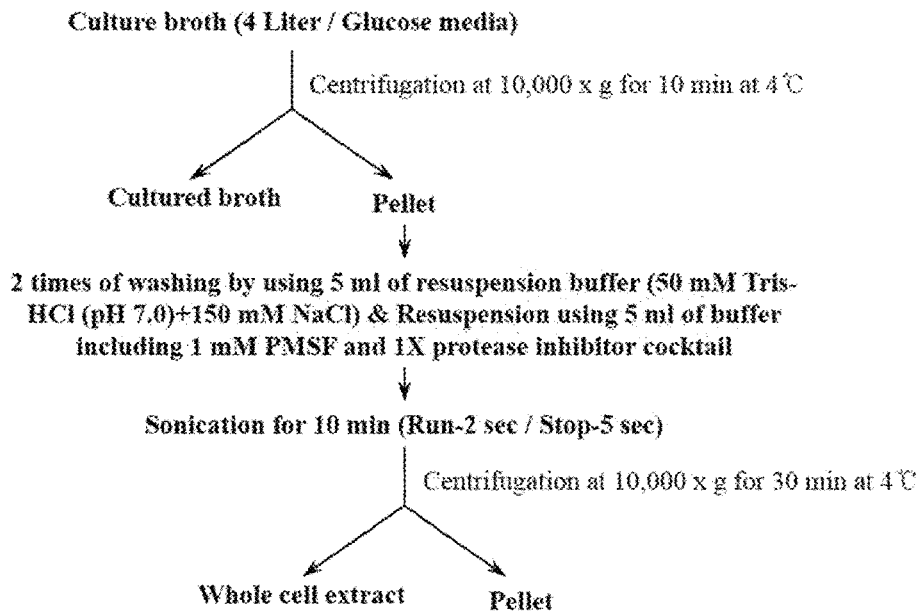

[Fig. 13]
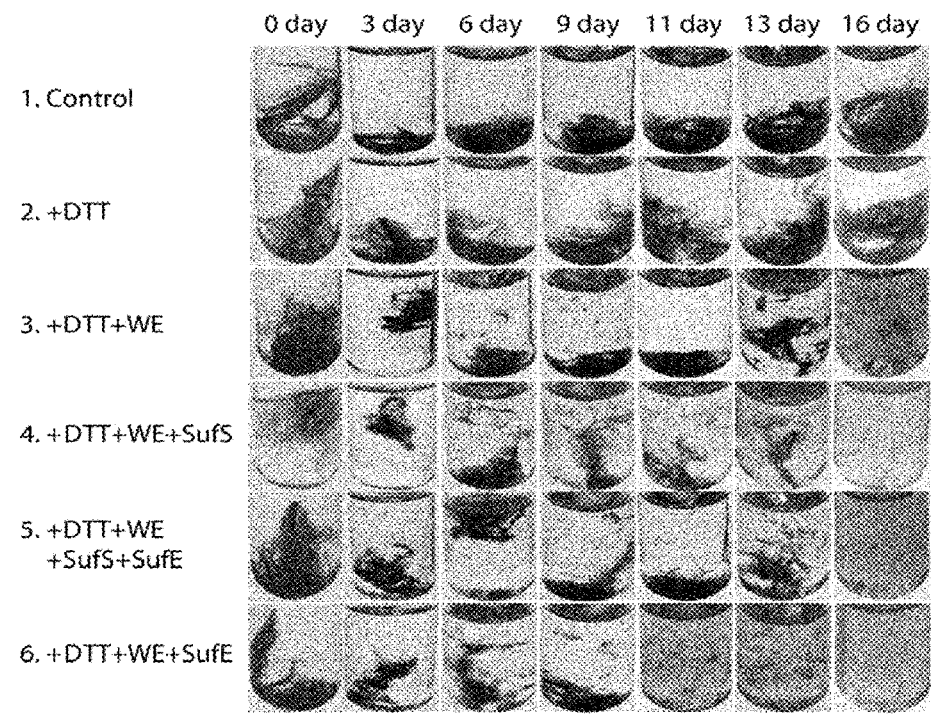
[Fig. 14]
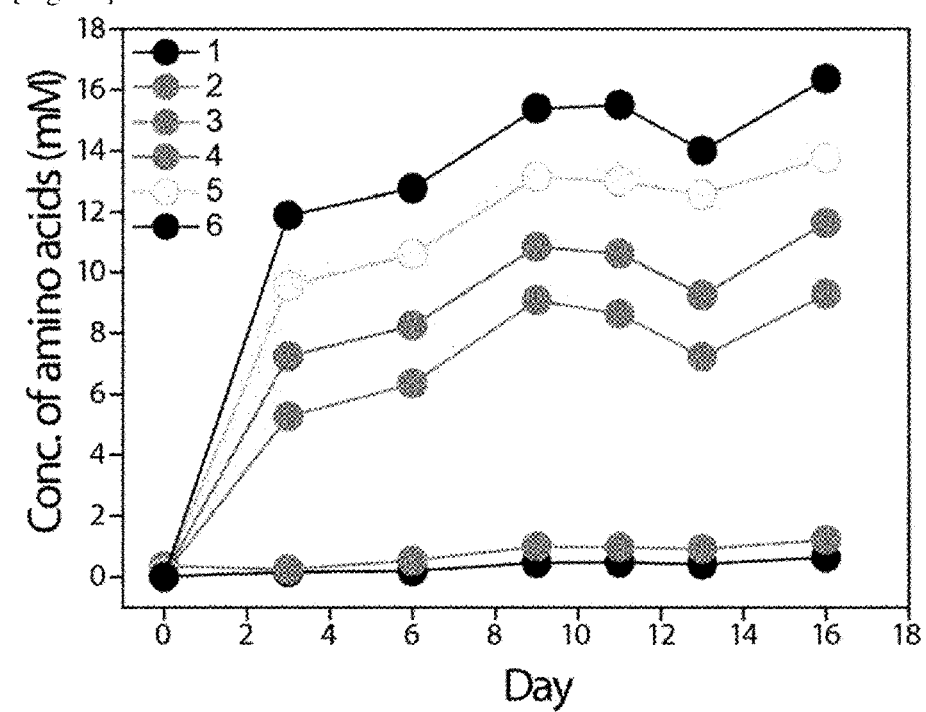

US 10,612,010 B2

THERMOPHILE-DERIVED KERATINASE AND USE THEREOF

TECHNICAL FIELD

The present invention relates to novel thermophile-derived keratin degrading enzymes.

Further, the present invention relates to polynucleotides encoding the keratin degrading enzymes, recombinant vectors containing the same, and host cells transformed by the recombinant vectors.

Further, the present invention relates to a method for preparing keratin degrading enzymes including a step of culturing the host cells.

Further, the present invention relates to a composition for keratin degradation containing the enzymes; and a method for decomposing keratin by using the same.

Further, the present invention relates to a keratin byproducts decomposed by the enzyme.

BACKGROUND ART

Keratin is an animal protein which is nutritionally valuable, but not widely used and a fibrous component of skin, horns and hair and has been wasted in bulk in the slaughter and cattle industry (Kornillowicz-Kowalska and Bohacz, 2011).

Since the keratin contains many disulfide bonds in its structure, the keratin has a water-insoluble characteristic and is not decomposed by general proteases (Onifade et al., 1998).

Currently, keratin wastes are incinerated or after the keratin is decomposed by chemical methods, the degradation product thereof is recycled as feed additives for livestock. The keratin decomposition product generated by chemical treatment has a high content of nitrogen, fat, and the like, but has disadvantages in that the content of amino acids such as lysine and methionine which are required for livestock is low and simultaneously, digestibility is low (Papadoulos and Ketelaars, 1986). Further, high energy cost is required and environmental problems such as odor can occur (da Rosa Gioppo and the like 2009). Therefore, in order to solve the problems, a new treatment method has been required and recently, a keratin decomposition method by microorganisms has been actively studied as an eco-friendly alternative to solve the above problems.

A microbiological keratin treatment method started with the isolation of microorganisms producing keratin degrading enzymes, and various microorganisms such as *Bacillus* spp., actinomycetes and fungi were isolated from a natural environment and enzyme production characteristics and the nutritional value of keratin decomposition products treated with these microorganisms have been reported (Bertsch and Coello, 2005; Brandelli, et al., 2010). In addition, it was reported that the keratinase can be used for removal of proteinaceous organic materials in a wastewater treatment plant, improvement of fabric quality, hair removal of leather, exfoliating cosmetics, prion decomposition, and the like (Gupta and Ramnani, 2006; Langeveld, et al., 2003; Onifade, et al., 1998). Further, in order to pioneer novel applications, studies for isolating strains having unique properties such as plant growth promoting activity and antifungal activity, together with keratinase activity have been started (Jeong, et al, 2010).

Meanwhile, it is known that coenzyme is more advantageous than using a purified enzyme to decompose proteins at low cost and the coenzyme is more stable than the purified enzyme. Actually, the product in the coenzyme state is commercialized as an enzyme preparation for treating a large amount of proteins. Further, since the characteristics of the keratinase are strain-specific, physicochemical properties of the enzymes produced by each strain need to be investigated for efficient application of the enzyme.

Technical Problem

The inventors of the present invention made every possible effort to find keratin degrading enzymes for effective decomposition and application of keratin to verify that thermophile-derived keratin degrading enzymes effectively decomposed the keratin and completed the present invention.

Accordingly, an object of the present invention is to provide a novel thermophile-derived keratin degrading enzymes.

Another object of the present invention is to provide polynucleotides encoding the keratin degrading enzymes, recombinant vectors containing the same, and host cells transformed by using the recombinant vectors.

Yet another object of the present invention is to provide a method for preparing keratin degrading enzymes including a step of culturing the host cells.

Still another object of the present invention is to provide a composition for keratin degradation containing the enzymes; and a method for decomposing keratin by using the same.

Still yet another object of the present invention is to provide a keratin byproducts decomposed by the enzymes.

Technical Solution

An aspect of the present invention provides thermophile-derived keratin degrading enzymes which contain at least more than one selected from a group consisting of:
 a cysteine desulfurase (CDS);
 a thermostable carboxypeptidase 1 (CBP);
 a thioredoxin-disulfide reductase (DSR); and
 an iron-sulfur assembly scaffold protein (SufE).

The cysteine desulfurase (CDS) may consist of an amino acid sequence of SEQ ID NO: 1;

The thermostable carboxypeptidase 1 (CBP) may consist of an amino acid sequence of SEQ ID NO: 3;

The thioredoxin-disulfide reductase (DSR) may consist of an amino acid sequence of SEQ ID NO: 5; and The iron-sulfur assembly scaffold protein (SufE) may consist of an amino acid sequence of SEQ ID NO: 7.

Further, the CDS, CBP, DSR, and SufE may be encoded by a polynucleotide consisting of
 a base sequence of SEQ ID NO: 2;
 a base sequence of SEQ ID NO: 4;
 a base sequence of SEQ ID NO: 6; and
 a base sequence of SEQ ID NO: 8.

In an embodiment of the present invention, cysteine desulfurase (CDS) which is present only in *Fervidobacterium islandicum* AW-1 and expected to be involved in decomposition of a chicken feather may be selected. The result is illustrated in FIG. 2. Further, the amino acid sequence information is designated as SEQ ID NO: 1 and the base sequence information is designated as SEQ ID NO: 2.

In the case of the thermostable carboxypeptidase 1 (CBP), comparison and analysis of amino acid sequence identity between proteases of *F. islandicum* AW-1 and proteases of *F. nodosum* Rt17-B1 which do not have the decomposition ability of the chicken feather wastes were performed by using a NCBI website-based blastp (blast.st-va.ncbi.nlm.nih.gov) program. The result is illustrated in FIG. 3.

As illustrated in FIG. 3, a protease thermostable carboxypeptidase 1 (CBP) which is expected to be involved in decomposition of a chicken feather wastes having low identity with the *F. nodosum* Rt17-B1 was finally screened.

The amino acid sequence information is designated as SEQ ID NO: 3 and the base sequence information is designated as SEQ ID NO: 4.

In the case of the thioredoxin-disulfide reductase (DSR), as a result of comparing and analyzing a genome with a *F. pennivorans* strain, which is known to have keratin decomposition capability in addition to the *F. islandicum* AW-1 by using a RAST server and a Bioedit analysis program, thioredoxin-disulfide reductase which has the highest amino acid identity and is expected to be involved in decomposition of chicken feather wastes was selected as illustrated in FIG. 4.

The amino acid sequence information was designated as SEQ ID NO: 5 and the base sequence information was designated as SEQ ID NO: 6.

In the case of the iron-sulfur assembly scaffold protein (SufE), it is expected that a complex with the CDS is formed to improve keratin decomposition capability. As a result, an iron-sulfur assembly scaffold protein which is demonstrated as present in a downstream of the CDS in a Suf operon through the RAST server was selected as illustrated in FIG. 5.

The amino acid sequence information was designated as SEQ ID NO: 7 and the base sequence information was designated as SEQ ID NO: 8.

Further, the thermophilic bacteria may be Thermotogales order.

The thermophilic bacteria are not limited as long as the thermophilic bacteria are included in the Thermotogales order, but for example, the Thermotogales order may be *Caldotoga, Mesotoga, Thermopallium, Thermotoga, Fervidobacterium, Thermosipho, Kosmotoga, Thermococcoides, Mariniloga, Geotoga*, or *Petrotoga* genus.

In an embodiment of the present invention, the *F. islandicum* AW-1-derived keratin degrading enzymes were used.

Further, another aspect of the present invention provides a polynucleotide encoding a keratinase which is at least one selected from a group consisting of: a cysteine desulfurase (CDS) consisting of an amino acid sequence of SEQ ID NO: 1;

a thermostable carboxypeptidase 1 (CBP) consisting of an amino acid sequence of SEQ ID NO: 3;

a thioredoxin-disulfide reductase (DSR) consisting of an amino acid sequence of SEQ ID NO: 5: and an iron-sulfur assembly scaffold protein (SufE) consisting of an amino acid sequence of SEQ ID NO: 7.

The polynucleotides encoding the CDS, CBP, DSR and SufE may be a base sequence of SEQ ID NO: 2;
a base sequence of SEQ ID NO: 4;
a base sequence of SEQ ID NO: 6; and
a base sequence of SEQ ID NO: 8, respectively.

The "polynucleotide" is a polymer of a deoxyribonucleotide or a ribonucleotide which is present in a form of a single strand or a double strand. The polynucleotide includes DNAs (gDNA and cDNA) and RNA sequences transcribed therefrom and includes analogs of natural polynucleotides unless specifically stated otherwise.

The polynucleotide includes not only a nucleotide sequence encoding the aforementioned peptide but also a complementary sequence to the sequence. The complementary sequence includes not only a complete complementary sequence but also a substantial complementary sequence.

Further, the polynucleotide may be modified. The modification includes addition, deletion, or non-conservative substitution or conservative substitution of the nucleotide. It is interpreted that the polynucleotide encoding the amino acid sequence includes a nucleotide sequence having substantial identity with respect to the nucleotide sequence. The substantial identity may be a sequence having identity and similarity of at least 60% and 80% in the case of analyzing a sequence which is aligned to maximally correspond to any different sequence from the nucleotide sequence and aligned by using an algorithm which is generally used in the related art.

Another aspect of the present invention provides a recombinant vector including the polynucleotide.

The term "vector" means a DNA molecule for expressing a target gene in host cells. For example, the vector includes plasmid vectors, cosmide vectors, and virus vectors such as bacteriophage vectors, adenovirus vectors, retrovirus vectors, and adeno-associated virus vectors. The vector which may be used as the recombinant vector may be prepared by manipulating plasmids (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, etc.), phages (for example, λgt4λB, λ-Charon, λΔz1, M13, etc.) or virus (for example, CMV, SV40, etc.), which are frequently used in the related art.

In the recombinant vector, the polynucleotide encoding the amino acid sequence may be operatively linked with the promoter. The term "operatively linked" means a functional binding between a regulatory sequence (e.g, a promoter sequence) and a different nucleotide sequence. Accordingly, the regulatory sequence may regulate transcription and/or translation of the different nucleotide sequence by the functional binding.

The recombinant vector may be typically constructed as a vector for cloning or a vector for expression. The expression vector may use general vectors which are used to express foreign proteins in plants, animals, or microorganisms in the art. The recombinant vector may be constructed by various methods known in the art.

The recombinant vector may be constructed using prokaryotic cells or eukaryotic cells as a host. For example, the used vector is an expression vector and in the case of using the prokaryotic cells as a host, the vector generally includes a strong promoter capable of processing a transcription (for example, a pLX promoter, a trp promoter, a lac promoter, a tac promoter, a T7 promoter, etc.), a ribosome binding site for initiation of translation, and a transcription/translation termination sequence. In the case of using the eukaryotic cells as a host, a replication origin that functions in the eukaryotic cells contained in the vector includes an f1 replication origin, an SV40 replication origin, a pMB1 replication origin, an adeno replication origin, an AAV replication origin, a CMV replication origin, a BBV replication origin, and the like, but is not limited thereto. Further, a promoter derived from a genome of mammalian cells (e.g., a metallothionine promoter) or a promoter derived from a mammalian virus (e.g., an adenovirus late-phase promoter, a vaccinia virus 7.5K promoter, an SV40 promoter, a cytomegalovirus (CMV) promoter and a tk promoter of HSV) may be used, and generally has a polyadenylation sequence as a transcription termination sequence.

Meanwhile, the vector may express not only a peptide specifically binding to NRP1 of the present invention but also fragments or an antibody of the antibody to which the peptide is fused. In the case of the antibody to which the peptide is fused or the fragments of the antibody, the vector may include a vector system in which the peptide and the antibody or its fragment are expressed at the same time in one vector or expressed in separate vectors respectively. In the case of being expressed in separate vectors, two vectors may be introduced to the host cells through co-transformation and targeted transformation.

Yet another aspect of the present invention provides host cells transformed by the recombinant vector.

The host cells may use any host cells known in the art, and as prokaryotic cells, for example, *E. coli* genus strains such as *E. coli* JM109, BL21, RR1, LE392, X1776 and W3110, *Bacillus* genus strains such as *Bacillus subtilis* and *Bacillus thuringiensis*, and Enterobacteriaceae and strains such as *Salmonella typhimurium, Serratia marcescens* and various *Pseudomonas* species are included. In the case of transformation to eukaryotic cells, as host cells, yeast (*Saccharomyce cerevisiae*), insect cells, plant cells and animal cells, for example, SP2/0, CHO (Chinese hamster ovary) K1, CHO DG44, PER.C6, W138, BHK, COS-7, 293, HepG2, Huh7, 3T3, RIN, MDCK cell lines, and the like may be used.

Still another aspect of the present invention provides a method for preparing the keratin degrading enzymes including a step of culturing the host cells.

An insertion method well-known in the field may be used for the insertion into the host cells of the polynucleotide or the recombinant vector containing the polynucleotide. The transfer method may use a $CaCl_2$) method or an electroporation method, or the like when the host cells are the prokaryotic cells, and use microinjection, calcium phosphate precipitation, electroporation, liposome-mediated transfection and gene bombardment when the host cells are eukaryotic cells, but is not limited thereto.

A method of screening the transformed host cells may be easily performed by using a phenotype expressed by a selection marker according to a method well-known in the art. For example, when the selection marker is a specific antibiotic resistance gene, a transformant may be easily screened by culturing the transformant in a medium containing the antibiotic.

Further, still yet another aspect of the present invention provides a composition for keratin decomposition including at least one thermophile-derived enzyme selected from a group consisting of:
a cysteine desulfurase (CDS);
a thermostable carboxypeptidase 1 (CBP);
a thioredoxin-disulfide reductase (DSR); and
an iron-sulfur assembly scaffold protein (SufE).

Further, still yet another aspect of the present invention provides a method for keratin decomposition including treating keratin with at least one thermophile-derived enzyme selected from a group consisting of:
a cysteine desulfurase (CDS);
a thermostable carboxypeptidase 1 (CBP);
a thioredoxin-disulfide reductase (DSR); and
an iron-sulfur assembly scaffold protein (SufE).

The cysteine desulfurase (CDS); the thermostable carboxypeptidase 1 (CBP); the thioredoxin-disulfide reductase (DSR); or the iron-sulfur assembly scaffold protein (SufE) may be supplementary or necessary in the decomposition of keratin.

The origin of the keratin is not limited. That is, the origin of the keratin may include hair, nails, animal hooves, skin, animal hair and feathers, and the like, and most preferably feathers.

Advantageous Effects

The keratin degrading enzymes according to the present invention rapidly and effectively decomposes hardly-decomposable keratin, and thus it is expected that the keratin degrading enzymes can be used for the effective wastes treatment and the transformation of agricultural and livestock wastes into high value-added resources, which causes environmental problems (for example, a novel material for enzyme cosmetics), and can be used in an innovative enzymatic bioconversion technique utilizing various decomposition enzyme groups.

DESCRIPTION OF DRAWINGS

FIG. 1 illustrates a result of analyzing genome information of *F. islandicum* AW-1 having keratin decomposition ability by using a RAST server.

FIG. 2 illustrates a cysteine desulfurase (CDS) screened as a keratin degrading enzymes group based on a result of comparing and analyzing protein function-based genomes.

FIG. 3 illustrates a thermostable carboxypeptidase 1 (CBP) screened as a keratin degrading enzymes group based on a result of comparing and analyzing amino acid sequence-based genomes.

FIG. 4 illustrates a thioredoxin-disulfide reductase (DSR) screened as a keratinase group based on a result of comparing and analyzing amino acid sequence-based genomes.

FIG. 5 illustrates an iron-sulfur assembly scaffold protein (SufE) screened as a keratinase group based on a result of comparing and analyzing amino acid sequence-based genomes.

FIG. 6 illustrates a schematic diagram of expression vectors of key proteins expected as a keratinase group.

FIG. 7 illustrates a biophysicochemical characteristic of a cysteine desulfurase (CDS) recombinant protein expected as a keratinase of *F. islandicum* AW-1.

FIG. 8 illustrates a biophysicochemical characteristic of a thermostable carboxypeptidase 1 (CBP) recombinant protein expected as a keratinase of *F. islandicum* AW-1.

FIG. 9 is a schematic diagram illustrating a method of extracting a whole cell extract for obtaining an enzyme group having keratin decomposition ability from *F. islandicum* AW-1.

FIG. 10 illustrates a result of verifying decomposition of a chicken feather wastes by using a whole cell extract and a recombinant protein of *F. islandicum* AW-1 having keratin decomposition ability.

FIG. 11 illustrates quantitative analysis of free amino acids produced by a decomposition experiment of the chicken feather wastes of FIG. 10.

FIG. 12 is a schematic diagram illustrating a method for extracting a whole cell extract extract from colonies in which *F. islandicum* AW-1 having keratin decomposition ability is anaerobically cultured in a medium added with 0.5% (v/v) glucose as a unique carbon source.

FIG. 13 illustrates a merge treatment effect for decomposition of the chicken feather wastes by selectively adding cysteine desulfurase (CDS) and iron-sulfur assembly scaffold protein (SufE) recombinant proteins in the whole cell extract of *F. islandicum* AW-1.

FIG. 14 is a graph illustrating a result of amino acids quantitative analysis of the decomposition effect of the chicken feather wastes by FIG. 13.

MODES OF THE INVENTION

Hereinafter, the present invention will be described in more detail through Examples. However, these Examples are to exemplify the present invention and the scope of the present invention is not limited to these Examples.

Experimental Example 1: Genome Analysis of *Fervidobacterium islandicum* AW-1

Colonies were collected from a culture broth of *F. islandicum* AW-1 having keratin decomposition ability to extract a genomic DNA by using a genomic DNA extraction kit (Solgent), and then obtain a genome base sequence by using a single molecule real-time (SMRT) sequencing platform (PacBio RS II system).

The genome information was analyzed by using a hierarchical genome-assembly process (RS-HGAP) assembly protocol and a RAST server (rast.nmpdr.org) in an SMRT analysis pipeline v.2.2.0. As a result, it was verified that a genome DNA size of *F. islandicum* AW-1 was 2.35 Mb and had 2,259 coding genes.

Experimental Example 2: Analysis of Comparing Protein Function-Based and Amino Acid Sequence-Based Genomes Using Genome Information of *Fervidobacterium islandicum* AW-1

A target enzyme group involved in keratin decomposition was selected by comparing and analyzing genome information of *F. islandicum* AW-1. To this end, proteins expected to be in the keratinase group, cysteine desulfurase (CDS), thermostable carboxypeptidase 1 (CBP), and thioredoxin-disulfide reductase (DSR) were selected by directly comparing and analyzing genome information with *F. islandicum* AW-1 having excellent keratin decomposition ability and strains corresponding to the same genus.

Particularly, in the case of the CDS, genomes of *Fervidobacterium islandicum* AW-1 as a chicken feather wastes decomposition strain and *F. nodosum* Rt17-B1 as a strain without chicken feather wastes decomposition ability were compared and analyzed based on a protein function by using the RAST server (rast.nmpdr.org). The result is illustrated in FIG. 2.

As illustrated in FIG. 2, cysteine desulfurase (CDS) which was present only in *F. islandicum* AW-1 and expected to be involved in decomposition of the chicken feather wastes was screened. The amino acid sequence information was designated as SEQ ID NO: 1 and the base sequence information was designated as SEQ ID NO: 2.

In the case of the thermostable carboxypeptidase 1 (CBP), comparison and analysis of amino acid sequence identities between proteases of *F. islandicum* AW-1 and proteases of *F. nodosum* Rt17-B1 as a strain without chicken feather wastes decomposition ability were performed by using a NCBI website-based blastp (blast.st-va.ncbi.nlm.nih.gov) program. The result was illustrated in FIG. 3.

As illustrated in FIG. 3, a protease thermostable carboxypeptidase 1 (CBP) which was expected to be involved in decomposition of the chicken feather wastes having low identity with the *F. nodosum* Rt17-B1 was finally screened.

The amino acid sequence information was designated as SEQ ID NO: 3 and the base sequence information was designated as SEQ ID NO: 4.

In the case of the thioredoxin-disulfide reductase (DSR), as a result of comparing and analyzing a genome with a *F. pennivorans* strain, which was known to have keratin decomposition ability in addition to the *F. islandicum* AW-1 by using a RAST server and a Bioedit analysis program, thioredoxin-disulfide reductase which had the highest amino acid identity and was expected to be involved in decomposition of a chicken feather wastes was screened as illustrated in FIG. 4.

The amino acid sequence information was designated as SEQ ID NO: 5 and the base sequence information was designated as SEQ ID NO: 6.

In the case of the iron-sulfur assembly scaffold protein (SufE), it was expected that a complex with the CDS was formed to increase keratin decomposition ability. As a result, an iron-sulfur assembly scaffold protein which was verified as present in a downstream of the CDS in a Suf operon through the RAST server was screened as illustrated in FIG. 5.

The amino acid sequence information was designated as SEQ ID NO: 7 and the base sequence information was designated as SEQ ID NO: 8.

Experimental Example 3: Preparation of Expression Vectors of CDS, CBP, and DSR Proteins and *E. coli* Transformants Expression vectors of proteins which were expected as a keratinase group screened by comparing and analyzing protein function-based and amino acid sequence-based genomes of *F. islandicum* AW-1 was prepared.

TABLE 1

| Sequence No. | Primer No. | Primer name | Primer base sequence (5'-3') |
|---|---|---|---|
| 9 | A | F.aw1_cds_NdeI F | CATATGCGCTCAACGG TGTTCTC |
| 10 | B | F.aw1_cds_XhoI R | CTCGAGTCATTCGAAC CACCTCC |
| 11 | C | F.aw1_cbp_NdeI F | CATATGGAAGAACTAA AAAGCTATTACAAACG |
| 12 | D | F.aw1_cbp_XhoI R | CTCGAGTTAAAGCTCT ATCTCATACACTTTG |
| 13 | E | F.aw1_dsr_NdeI F | CATATGAGCGGATTTG AATTCGACA |
| 14 | F | F.aw1_dsr_XhoI R | CTCGAGTTAGAAGTAT TTCTTTGCAGCG |
| 15 | G | F.aw1_sufE_NdeI F | GCGCATATGATATACT CTGAATTCATAATGG |
| 16 | H | F.aw1_sufE_XhoI R | CTCGAGTAATTCATTC TTTAAAGCAATCTCC |

As shown in Table 1, in order to prepare expression vectors CDS, CBP, DSR, and SufE, first, forward primers and reverse primers containing respective restriction enzymes sequence (NdeI or XhoI) were used in pairs in PCR according to the preparation of the expression vectors.

A genomic DNA of the *Fervidobacterium islandicum* AW-1 strain was used as a template for the amplification of each gene by the PCR method, and the reaction was performed at 98° C. for 5 min using Primestar HS DNA polymerase from Takara Corporation, performed at 98° C. for 30 s, 55° C. for 15 s, and 72° C. for 1 min by 30 cycles, and then performed at 72° C. for 10 min.

The amplified PCR product was electrophoresed and isolated and purified by using a gel extraction kit (QIAGEN), cloned by using a pTOP Blunt V2 cloning kit (Enzynomics), and then whether to insert a mutant of each gene was verified through DNA sequencing (Solgent).

A pET-28a (+) (Novagen) vector was treated with restriction enzymes NdeI and XhoI for the preparation of each gene expression vector after verifying that there was no mutant in three kinds of genes expected as a keratinase group obtained through the PCR. For the recovery of each gene cloned in the pTOP Blunt V2 vector, the restriction enzyme corresponding to the expression vector was treated and isolated and purified by using electrophoresis and the gel extraction kit (QIAGEN).

Four kinds of expression vectors pET28a-CDS, pET28a-CBP, pET28a-DSR, and pET28a-SufE were prepared by ligating the restriction enzyme-treated vector and the recovered genes by using a DNA ligation kit (Takara). A cleavage map of the expression vectors was illustrated in FIG. 6. For expression of protein genes expected as a keratinase group, *E. coli* transformants were prepared as follows. Each expression vector plasmid was introduced into an *E. coli* strain BL21 (DE3) (Enzynomics). In order to selectively culture the transformants, an LB solid medium containing kanamycin, was cultured at 37° C. Kanamycin is an antibiotic suitable for the antibiotic resistance gene contained in the expression vector. The final concentration of kanamycin was 100 μg/ml.

Experimental Example 4: Mass Expression and Purification of Proteins CDS, CBP, DSR, and SufE For expression of protein genes expected as the keratinase group, transformants into which each expression vector was inserted was obtained and then used. Each transformant was pre-cultured and then 1% (5 ml) of pre-cultured cells were inoculated and cultured in 500 ml of a LB added with kanamycin (100 μg/ml) in two 2 L flasks. An isopropyl β-D-1-thiogalactopyranoside (IPTG) at a final concentration of 1 mM was added when absorbance (600 nm) was 0.4 to 0.6, expression of the CDS, CBP, DSR and SufE genes was induced at 37° C. for 6 h.

Cells induced by protein expression were centrifuged after a culture broth with absorbance (600 nm) 1 was transferred to a 1.5 ml E-tube and then only cultured colonies were recovered. The cells were suspended in 100 μl of a 1×SDS sample buffer and treated in boiled water for 5 min, modified and isolated by a 12% sodium dodecyl sulphate-polyacrylamide gel electrophoresis (SDS-PAGE) gel and then stained with coomassie brilliant blue (CBB) R-250, and then protein expression levels were confirmed. The cultured cells were recovered by centrifugation and resuspended in 50 mM Tris-HCl (pH 7.0) containing 150 mM NaCl and 1 mM phenylmethylsulfonyl fluoride (PMSF). The cells were broken by sonication at 4° C. and the supernatant was recovered by centrifugation (10,000×g, 20 min).

The recovered supernatant was heat-treated (70° C. for 30 min), centrifuged (10,000×g, 20 min) and 0.45 μm-filtered to obtain a sample for His-tag purification. As a next step, in order to purify each expression protein, the expression protein was isolated and purified by using $Ni^{2+}$-NTA agarose beads (Novagen). The expression protein containing a 6-histidine residue in an N-terminus was bound through the $Ni^{2+}$-NTA agarose beads equilibrated with a binding buffer (0.5 M NaCl, 20 mM Tris-HCl (pH 7.9), 5 mM imidazole), nonspecific binding proteins were removed by using a washing buffer (0.5 M NaCl, 20 mM Tris-HCl (pH 7.9), 60 mM imidazole), and then finally, target proteins bound to beads were eluted with an elution buffer (0.5 M NaCl, 20 mM Tris-HCl (pH 7.9), 250 mM imidazole) and the expressed proteins were His-tag-purified.

Since all of the purified proteins were His-tagged at the N-terminus, thrombin (1.6 unit/μl) as a protease was treated to recover the protein in which the tag was removed. After thrombin treatment, gel filtration was performed using a HiLoad 16/60 superdex 200 prep grade column (GE healthcare) and finally, the proteins were recovered and used in a decomposition experiment for the chicken feather wastes. In the case of the CBP, after the His-tag purification, except for the process of treating the protease, the gel filtration was directly performed and finally used for the decomposition experiment for the chicken feather wastes.

Experimental Example 5: Analysis of Biochemical Characteristics of Proteins CDS and CBP As illustrated in FIGS. 7 and 8, characteristics of recombinant proteins CDS and CBP of *F. islandicum* AW-1 strains were analyzed. In the case of the CDS, an optimal enzyme addition amount, a substrate mass and an optimal reaction time were determined by using a methylene blue assay, and then maximum enzyme activity was shown at 90° C. and pH 8.0, respectively, as illustrated in FIG. 7. As the result of verifying the kinetics of the enzyme, it was verified that $V_{max}$ was 1135.0±11.0 (Unit/mg) and $K_m$ was 75.0±1.7 μmol. In the case of the CBP, an optimal enzyme addition amount, a substrate mass and an optimal reaction time were determined by using a ninhydrin assay, and then maximum enzyme activity was shown at 80° C. and pH 7.0, respectively, as illustrated in FIG. 8. Further, considering that metal ions affected CBP activity, it was confirmed that the activity of the CBP was increased four times or more under presence of cobalt ion ($Co^{2+}$).

Experimental Example 6: Protein Fractionation of *Fervidobacterium Islandicum* AW-1 Strain As shown in FIG. 9, cells of *F. islandicum* AW-1 having keratin decomposition ability were recovered from a culture broth (4 liters) containing the chicken feather wastes and grinded, and then a whole cell extract (Table 2) was obtained through protein fractionation and used for the decomposition experiment of the chicken feather wastes.

TABLE 2

|  | Protein conc. (mg/ml) | Volume (ml) | Total amount (mg) |
| --- | --- | --- | --- |
| Whole cell extract | 3.96 | 5 | 19.81 |
| Pellet | 2.39 | 5 | 11.95 |
| Cytosol | 2.33 | 4.3 | 9.997 |
| Membrane protein | 5.86 | 1 | 5.86 |
| Solubilized membrane | 1.91 | 1.1 | 2.10 |
| Pellet membrane | 3.68 | 1 | 3.68 |

Experimental Example 7: Decomposition Experiment of Chicken Feather Wastes Using Whole Cell Extract and Recombinant Protein The decomposition experiment of the chicken feather wastes was performed as follows by using the whole cell extract and the recombinant proteins CDS, CBP, and DSR of *F. islandicum* AW-1. The chicken feather wastes (10 mg) was added in a Hungate tube and 5 ml of a 50 mM HEPES buffer (pH 8.0) containing 0.05 mg of resazurin was dispensed. After replacing nitrogen gas for 10 min, a tube was sealed with a rubber stopper and an aluminum seal, and sterilized at 121° C. for 20 min, and then after cooling, 10 μl of Na₂S was added to each sterilized tube. The whole cell extract and the recombinant proteins CDS, CBP and DSR were diluted with a 50 mM HEPES buffer (pH 8.0) and then 0.2 mg was used. Dithiothreitol (DTT), a reducing agent, was used to be a final 10 mM. Each enzyme reaction (see Table 3) was shaken 2-3 times and then performed in a water bath at 80° C.

TABLE 3

| Reaction condition No. | Reducing agent DTT (10 mM) | Whole cell extract supernatant | Whole cell extract solublized cytosol | Whole cell extract membrane | Recombinant protein CDS | Recombinant protein CBP | Recombinant protein DSR |
|---|---|---|---|---|---|---|---|
| 1 | x | x | x | x | x | x | x |
| 2 | x | o | x | x | x | x | x |
| 3 | o | o | x | x | x | x | x |
| 4 | x | x | o | x | x | x | x |
| 5 | o | x | o | x | x | x | x |
| 6 | x | x | x | o | x | x | x |
| 7 | o | x | x | o | x | x | x |
| 8 | x | x | o | x | x | x | o |
| 9 | o | x | x | x | o | o | o |
| 10 | x | x | x | x | o | o | o |
| 11 | o | x | o | x | o | x | x |
| 12 | o | x | o | x | x | x | o |
| 13 | o | x | o | x | x | o | x |
| 14 | o | x | 0.05 mg | x | x | x | x |
| 15 | o | x | 0.1 mg | x | x | x | x |

(o: added enzyme, x: non-added enzyme)

As illustrated in FIG. 10, the decomposition forms of the chicken feather wastes was verified at a 24-hour unit, and finally, amino acid quantification was performed by a ninhydrin assay by using a culture medium for 72 h and the result was shown in FIG. 11. The ninhydrin assay was performed by adding the same amount of 10% trichloroacetic acid (TCA) solution to 50 μl of a culture broth recovered under each reaction condition and then vortexing, and a supernatant recovered through centrifugation at 13,000 rpm for 10 min was added with 15 μl of a 3% ninhydrin solution and 150 μl of an acetate cyanide buffer. The supernatant was boiled for 15 min and added with 660 μl of a pre-chilled isopropanol-water diluent, and then voltexing was performed and absorbance was measured at 570 nm by using an Ultraspec 8000 spectrophotometer (GE healthcare).

As the result of this experiment, the decomposition of the chicken feather wastes was verified in all of the whole cell extracts of the *F. islandicum* AW-1 strain having keratin decomposition ability, and the decomposition of the chicken feather wastes was confirmed in the reaction of adding both the whole cell extract and the recombinant protein. In addition, as a result of verifying a minimum amount of whole cell extract for the decomposition of 10 mg of chicken feather wastes (No. 14, 15), it was confirmed that a minimum of 0.05 mg of the whole cell extract was required.

Experimental Example 8: Decomposition Experiment for Chicken Feather Wastes Using Whole Cell Extract and Recombinant Proteins CDS and SufE of Colonies Cultured by Adding Glucose As illustrated in FIG. 12, *F. islandicum* AW-1 cell having keratin decomposition ability was grinded in a culture broth added with 0.5% (v/v) glucose instead of the chicken feather wastes and then a whole cell extract was obtained and used in the decomposition experiment for the chicken feather wastes. The chicken feather wastes (10 mg) was added to a Hungate tube for the decomposition experiment of the chicken feather wastes by adding the whole cell extract and the recombinant protein SufE and a 50 mM HEPES buffer (pH 8.0) containing 50 mg of resazurin was dispensed by 5 ml. After replacing nitrogen gas for 10 min, a tube was sealed with a rubber stopper and an aluminum seal, and sterilized at 121° C. for 20 min, and then after cooling, 10 μl of Na₂S was added to each sterilized tube. The whole cell extract, 0.5 mg of the recombinant protein CDS, and 2.5 mg of the recombinant protein SufE were used. Dithiothreitol (DTT), a reducing agent, was used to be a final 10 mM. The enzyme was added to each Hungate tube prepared in an anaerobic chamber under each condition (see Table 4), shaken several times, and then the reaction was started at 80° C. in a water bath.

TABLE 4

| Reaction condition No. | Reducing agent DTT (10 mM) | Whole cell extract whole cell extract | Recombinant protein CDS | Recombinant protein SufE |
|---|---|---|---|---|
| 1 | x | x | x | x |
| 2 | o | x | x | x |
| 3 | o | o | x | x |
| 4 | o | o | o | x |
| 5 | o | o | o | o |
| 6 | o | o | x | o |

(o: added enzyme, x: non-added enzyme)

As illustrated in FIG. 13, the decomposition pattern of the chicken feather wastes was verified by a 3-day unit and finally, quantification of amino acid was performed by a ninhydrin assay using the sampled culture broth. The result was shown in FIG. 14. The ninhydrin assay was performed by adding the same amount of 10% TCA solution to 50 μl of a culture solution recovered under each reaction condition and then vortexing, and 30 μl of a supernatant recovered through centrifugation at 13,000 rpm for 10 min was added with 150 μl of a 3% ninhydrin solution and 150 μl of an acetate cyanide buffer. The supernatant was boiled for 15 min after voltexing and added with 660 μl of a pre-chilled isopropanol-water diluent, and then voltexing was performed and absorbance was measured at 570 nm by using an Ultraspec 8000 spectrophotometer (GE healthcare).

As a result of this experiment, even in the whole cell extract of the *F. islandicum* AW-1 strain having keratin decomposition capability cultured in a medium added with glucose instead of the chicken feather, the chicken feather wastes decomposition was verified, and even in a reaction of adding both the whole cell extract and the recombinant protein, the decomposition of the chicken feather wastes was confirmed. In addition, in the case of using the whole cell extract derived from the glucose medium, compared with the case of using the whole cell extract derived from the chicken feather medium, it was demonstrated that the decomposition of the chicken feather wastes was slower and herein, it was demonstrated that when the recombinant proteins CDS and SufE were added, the chicken feather decomposition speed was faster.

The invention claimed is:

1. A method for keratin decomposition comprising, a step of treating keratin with
   i) at least one Thermotogales order derived enzyme or protein selected from the group consisting of:
   an isolated cysteine desulfurase (CDS);
   an isolated thermostable carboxypeptidase 1 (CBP);
   an isolated thioredoxin-disulfide reductase (DSR); and
   an isolated iron-sulfur assembly scaffold protein (SufE); and also
   ii) a Thermotogales order-derived cell extract,
   wherein (i) and (ii) are not the same.

2. The method for keratin decomposition of claim 1, wherein the keratin is derived from poultry feathers.

3. The method for keratin decomposition of claim 1, wherein the isolated cysteine desulfurase (CDS) consists of the amino acid sequence of SEQ ID NO: 1; the isolated thermostable carboxypeptidase 1 (CBP) consists of the amino acid sequence of SEQ ID NO: 3; the isolated thioredoxin-disulfide reductase (DSR); consists of the amino acid sequence of SEQ ID NO: 5; and the isolated iron-sulfur assembly scaffold protein (SufE) consists of the amino acid sequence of SEQ ID NO: 7.

4. The method for keratin decomposition of claim 1, wherein the CDS, CBP, DSR, and SufE are encoded by a polynucleotide consisting of
   the base sequence of SEQ ID NO: 2;
   the base sequence of SEQ ID NO: 4;
   the base sequence of SEQ ID NO: 6; and
   the base sequence of SEQ ID NO: 8, respectively.

5. The method for keratin decomposition of claim 1, wherein the Thermotogales order includes *Caldotoga*, *Mesotoga*, *Thermopallium*, *Thermotoga*, *Fervidobacterium*, *Thermosipho*, *Kosmotoga*, *Thermococcoides*, *Marinitoga*, *Geotoga*, or *Petrotoga* genus.

6. The method for keratin decomposition of claim 1, further, comprising the step of treating the keratin with Dithiothreitol.

7. The method for keratin decomposition of claim 1, wherein the Thermotogales order is *Fervidobacterium islandicum* AW-1 strain.

* * * * *

SEQUENCE LISTING

<160> NUMBER OF SEQ ID NOS: 16

<210> SEQ ID NO 1
<211> LENGTH: 421
<212> TYPE: PRT
<213> ORGANISM: Artificial Sequence
<220> FEATURE:
<223> OTHER INFORMATION: amino acid sequences of Cysteine desulfurase
       (CDS)

<400> SEQUENCE: 1

Met Arg Ser Thr Val Phe Ser Asp Glu Glu Phe Ser Asn Ile Leu Asn
1               5                   10                  15

Asp Phe Pro Ala Leu Lys Arg Asn Ile Asn Gly Lys Arg Leu Val Tyr
            20                  25                  30

Leu Asp Asn Ala Ala Ser Thr Leu Lys Cys Lys Ser Val Ile Glu Lys
        35                  40                  45

Met Thr Asp Phe Tyr Leu Tyr His Tyr Ser Asn Ile His Arg Ala Val
    50                  55                  60

His Thr Leu Ala Ser Glu Ala Thr Val Ala Tyr Glu Gln Ala Arg Glu
65                  70                  75                  80

Lys Val Ala Asn Phe Leu Asn Ala Ser Ser Glu Glu Ile Ile Phe Thr
                85                  90                  95

Ser Gly Thr Thr Met Gly Ile Asn Phe Leu Val Asn Ser Leu Ala Lys
            100                 105                 110

Ser Gly Ile Leu Lys Thr Glu Asp Thr Val Leu Ile Ser Gln Val Glu
        115                 120                 125

His His Ala Asn Leu Val Pro Trp Val Arg Leu Ser Lys Phe Tyr Gly
    130                 135                 140

Phe Lys Val Ala Tyr Ile Thr Ala Asp Glu Lys Gly Val Ile Thr Asn
145                 150                 155                 160

Glu Ser Ile Leu Lys Thr Lys Glu Ser Ile Pro Asn Pro Lys Val Val
                165                 170                 175

Ser Ile Thr Gly Gln Ser Asn Val Thr Gly Gln Glu Met Pro Ile Glu
            180                 185                 190

Leu Ile Arg Glu Thr Phe Lys Asn Ala Thr Leu Ile Val Asp Gly Ala
        195                 200                 205

Gln Leu Val Pro His Lys Lys Val Asp Val Lys Lys Leu Asp Val Asp
    210                 215                 220

Phe Leu Val Phe Ser Gly His Lys Ile Leu Gly Pro Thr Gly Ile Gly
225                 230                 235                 240

Val Leu Tyr Gly Lys Lys Ala Leu Leu Glu Gln Leu Glu Pro Phe Leu
                245                 250                 255

Tyr Gly Gly Glu Met Ile Asp Lys Val Thr Phe Glu Asp Val Thr Phe
            260                 265                 270

Asn Val Leu Pro Tyr Arg Phe Glu Ala Gly Thr Gln His Ile Thr Gly
        275                 280                 285

Ala Val Gly Leu Gly Tyr Thr Ile Asp Tyr Leu Glu Ser Ile Gly Phe
    290                 295                 300

Glu Lys Val Glu Lys His Val Glu Glu Leu Ser Asn Tyr Leu Leu Glu
305                 310                 315                 320

Lys Met Met Glu Leu Asp Phe Val Glu Val Tyr Gly Pro Ile Asp Ser
                325                 330                 335

Ser His Lys Ser Leu Val Ser Phe Asn Val Lys Gly Val His Pro His
            340                 345                 350

```
Asp Val Ser His Ile Leu Asp Glu Asn Phe Gly Val Ala Thr Arg Ser
            355                 360                 365

Gly His His Cys Ala Gln Pro Leu Met Gly Val Leu Ala Lys Gly Ser
        370                 375                 380

Lys Ile Asp Phe Pro Asn Ser Thr Val Arg Ala Ser Val Tyr Leu Tyr
385                 390                 395                 400

Asn Thr Lys Glu Asp Ile Asp Val Leu Ile Glu Gly Leu Lys Tyr Ile
            405                 410                 415

Arg Arg Trp Phe Glu
            420

<210> SEQ ID NO 2
<211> LENGTH: 1266
<212> TYPE: DNA
<213> ORGANISM: Artificial Sequence
<220> FEATURE:
<223> OTHER INFORMATION: nucleic acid sequences of Cysteine desulfurase
      (CDS)

<400> SEQUENCE: 2
atgcgctcaa cggtgttctc ggatgaggag ttttcaaata tactgaacga ttttcctgca      60
cttaaaagaa atatcaacgg caagaggtta gtttatttag ataatgcagc aagcacgctc    120
aaatgcaaat ccgtcatcga aaagatgacg gattttacc tttatcatta ttccaacatc     180
cacagagctg ttcacacact cgcaagtgag gcaacagtcg cgtacgaaca agcaagggaa    240
aaagtggcca ttttttgaa cgcaagttcc gaagaaatca tcttcacaag tggaacaact    300
atgggaataa atttcttagt gaactcgctc gcgaaaagcg ggattttgaa acggaagat    360 actgtattaa tttcacaagt agaacaccat gcgaatctcg taccttgggt gagactctca    420
aaattctacg gctttaaagt agcttacata acggcagatg aaaaagggt tatcacaaat    480 gaatcaattt tgaaaactaa agaatctatt ccaaacccaa agttgtttc aattacagga    540 cagtcaaatg ttacaggtca agagatgcct atagagttga taagagagac tttcaaaaat    600
gcaaccttga tagttgacgg tgctcagctt gtaccacata aaaaagttga tgtcaaaag    660 ctcgatgttg attttctcgt gttttcaggc cacaaaatac ttggcccgac gggaataggt    720
gttctgtatg gaaaaaaggc acttcttgaa cagcttgagc cgttttttgta cggcggggag    780 atgatagata agttacatt cgaagatgtt acattcaatg ttctaccgta cagattcgaa    840
gccggtactc aacacatcac aggtgccgtt gggcttggtt atacgataga ttatctggaa    900
agtatcggat tgagaaggt agaaaagcac gttgaagagt tatcaaatta cctgttagaa    960
aagatgatgg aacttgattt tgtggaagtc tacggaccaa ttgattcttc tcacaaatct    1020
ttggtatcat taatgtgaa aggtgtgcat ccgcatgatg tttcacacat actcgatgag    1080
aattttggtg tagccacaag aagcgggcac cattgtgcac aaccgctaat gggcgtctta    1140
gcgaaaggat caaagataga ttttcctaac tcaacagtta gagcgagcgt tatctatac    1200 aacacgaaag aagatataga tgtcttaata gaagggttaa atacatccg gaggtggttc    1260 gaatga                                                              1266

<210> SEQ ID NO 3
<211> LENGTH: 489
<212> TYPE: PRT
<213> ORGANISM: Artificial Sequence
<220> FEATURE:
<223> OTHER INFORMATION: amino acid sequences of Thermostable
      carboxypeptidase 1 (CBP1)
```

<400> SEQUENCE: 3

```
Met Glu Glu Leu Lys Ser Tyr Tyr Lys Arg Val Ala Lys Tyr Tyr Ser
1               5                   10                  15

Ala Ala Ala Leu Leu Tyr Trp Asp Met Gln Thr Tyr Met Pro Lys Asp
            20                  25                  30

Ala Gly Pro Tyr Arg Ala Glu Val Leu Ser Glu Ile Gly Thr Tyr Ala
        35                  40                  45

Phe Lys Gln Ile Thr Asp Asp Ala Leu Gly Lys Leu Leu Glu Thr Ala
    50                  55                  60

Gln Pro Gln Ser Glu Ile Asp Glu Lys Leu Val Tyr Val Gly Lys Lys
65                  70                  75                  80

Glu Tyr Tyr Lys Tyr Lys Lys Val Pro Pro Glu Leu Phe Gln Glu Ile
                85                  90                  95

Met Ile Thr Ser Thr Met Leu Glu Gln Lys Trp Glu Ile Ala Lys Pro
            100                 105                 110

Arg Gly Asp Phe Glu Glu Val Arg Pro Leu Leu Glu Lys Ile Val Asp
        115                 120                 125

Leu Ser Arg Lys Tyr Ala Asp Ile Leu Gly Tyr Glu Gly Glu Pro Tyr
    130                 135                 140

Asn Ala Leu Leu Asp Leu Tyr Glu Pro Gly Met Lys Ala Glu Glu Val
145                 150                 155                 160

Asp Gln Ile Phe Ser Lys Val Arg Asp Phe Ile Val Glu Val Leu Glu
                165                 170                 175

Lys Ile Glu Arg Leu Pro Lys Ser Glu Asp Pro Phe Asn Arg Glu Ile
            180                 185                 190

Gly Val Asp Lys Gln Lys Glu Phe Ser Asn Trp Leu Leu His Tyr Leu
        195                 200                 205

Lys Tyr Asp Phe Thr Lys Gly Arg Leu Asp Val Ser Ala His Pro Phe
    210                 215                 220

Thr Asn Pro Ile Gly Leu Asn Asp Val Arg Ile Thr Thr Arg Tyr Ile
225                 230                 235                 240

Val Asn Asp Ile Arg Asn Ser Ile Tyr Ser Thr Ile His Glu Phe Gly
                245                 250                 255

His Ala Leu Tyr Ala Leu Ser Ile Pro Thr Glu Phe Tyr Gly Leu Pro
            260                 265                 270

Ile Gly Ser Ser Ala Ser Tyr Gly Phe Asp Glu Ser Gln Ser Arg Phe
        275                 280                 285

Trp Glu Asn Val Val Gly Arg Ser Leu Ala Phe Trp Lys Gly Ile Tyr
    290                 295                 300

Ser Lys Phe Ile Glu Ile Val Pro Glu Met Arg Gly Tyr Ser Val Glu
305                 310                 315                 320

Glu Leu Trp Arg Ala Val Asn Arg Val Gln Arg Ser Phe Ile Arg Thr
                325                 330                 335

Glu Ala Asp Glu Val Thr Tyr Asn Leu His Ile Ile Arg Phe Glu
            340                 345                 350

Ile Glu Arg Glu Leu Ile Asn Gly Glu Leu Ser Val Lys Asp Val Pro
        355                 360                 365

Asp Lys Trp Asn Glu Leu Tyr Lys Lys Tyr Leu Gly Leu Asp Val Pro
    370                 375                 380

Asn Asn Thr Leu Gly Cys Met Gln Asp Pro His Trp Phe Gly Gly Asn
385                 390                 395                 400

Phe Gly Tyr Phe Pro Thr Tyr Ala Leu Gly Asn Leu Tyr Ala Ala Gln
                405                 410                 415
```

```
Ile Phe Glu Lys Leu Lys Glu Glu Ile Asn Phe Glu Val Val Ser
        420                 425                 430

Ala Gly Asn Phe Glu Ile Ile Lys Asn Phe Leu Lys Glu Lys Ile His
        435                 440                 445

Ser Lys Gly Lys Met Tyr Glu Pro Ser Asp Leu Ile Lys Ile Val Thr
450                     455                 460

Gly Lys Pro Leu Ser Tyr Glu Ser Phe Val Arg Tyr Ile Lys Asp Lys
465                 470                 475                 480

Tyr Ser Lys Val Tyr Glu Ile Glu Leu
                485

<210> SEQ ID NO 4
<211> LENGTH: 1470
<212> TYPE: DNA
<213> ORGANISM: Artificial Sequence
<220> FEATURE:
<223> OTHER INFORMATION: nucleic acid sequences of Thermostable
      carboxypeptidase 1 (CBP1)

<400> SEQUENCE: 4
```

| | | | | | |
|---|---|---|---|---|---|
| atggaagaac | taaaaagcta | ttacaaacgt | gtcgctaagt | actacagcgc | agccgcattg | 60 |
| ctttactggg | atatgcaaac | gtatatgcca | aaagatgcag | gaccgtacag | agcggaagtg | 120 |
| ctatcggaaa | ttggaacgta | cgcttttaaa | caaataactg | acgacgctct | cggaaaactg | 180 |
| ttggaaacag | ctcaaccaca | aagtgaaatc | gacgagaagc | tagtctatgt | aggaaagaag | 240 |
| gaatactaca | agtacaaaaa | agttcctcct | gaactatttc | aagagattat | gataacatca | 300 |
| acaatgctag | agcaaaagtg | ggaaattgct | aaaccgcgtg | gtgatttcga | agaagtaaga | 360 |
| cctttgcttg | aaaaaattgt | cgatctcagt | agaaaatacg | cagacatttt | aggttacgaa | 420 |
| ggtgaaccgt | acaacgcgtt | actcgaccta | tacgaacccg | gaatgaaggc | agaagaagtg | 480 |
| gatcagatat | tcagtaaagt | cagagatttt | atagtggaag | tgctcgaaaa | atcgaaaggg | 540 |
| ttgccaaaat | cagaggatcc | gttcaataga | gaaatcgggg | tagataagca | aaaagaattc | 600 |
| agcaactggc | tgcttcacta | tctcaagtac | gattttacca | agggaaggtt | ggatgtatca | 660 |
| gcgcatcctt | tcaccaatcc | aataggtcta | acgatgtac | gcataacaac | aaggtacata | 720 |
| gttaatgaca | tcagaaattc | catatactct | acgatacacg | aatttgggca | cgcactgtac | 780 |
| gcactttcaa | ttcctaccga | gttctacggt | ctaccaattg | gtagcagcgc | ctcatacggt | 840 |
| ttcgacgaga | gtcaatcgcg | cttttgggaa | aatgtagttg | gcagaagctt | ggcattttgg | 900 |
| aaagggattt | atagcaaatt | catagaaatt | gttcccgaga | tgcggggata | ttcggttgaa | 960 |
| gaattatgga | gggcggtgaa | cagagtccaa | aggtcgttca | ttagaaccga | agcggacgaa | 1020 |
| gttacgtaca | acctgcacat | aatcatccgt | tttgagattg | aacgcgagct | aatcaacggt | 1080 |
| gaactgagtg | ttaaagacgt | cccagacaag | tggaacgagc | tctacaaaaa | atacctgggg | 1140 |
| ctggatgtgc | caaacaatac | gcttggttgt | atgcaagatc | cacattggtt | cggcgggaat | 1200 |
| tttggttatt | ttccaactta | tgcacttggc | aacctttatg | ctgctcagat | atttgaaaaa | 1260 |
| ttaaaagaag | aaataaactt | tgaagaagtt | gtttcagctg | gtaattttga | gatcattaaa | 1320 |
| aacttcctga | agagaagat | ccattcgaag | ggtaaaatgt | acgaaccaag | cgacttgatt | 1380 |
| aaaatcgtga | ctggcaaacc | gctgtcttac | gaatctttcg | tgagatacat | taaggataag | 1440 |
| tactccaaag | tgtatgagat | agagctttaa | | | | 1470 |

<210> SEQ ID NO 5

<211> LENGTH: 318
<212> TYPE: PRT
<213> ORGANISM: Artificial Sequence
<220> FEATURE:
<223> OTHER INFORMATION: amino acid sequences of Thioredoxin-disulfide reductase (CDR)

<400> SEQUENCE: 5

Met Ser Gly Phe Glu Phe Asp Met Gly Ser Phe Gly Gly Asn Leu Lys
1               5                   10                  15

Glu Tyr Tyr Asp Ile Ala Ile Ile Gly Gly Pro Ala Gly Leu Thr
            20                  25                  30

Ala Ala Ile Tyr Ala Arg Arg Ala Gly Leu Thr Ala Leu Val Ile Glu
        35                  40                  45

Lys Ala Ile Glu Gly Gly Ala Val Thr Gln Thr His Val Val Glu Asn
50                  55                  60

Trp Pro Gly Glu Ile Ser Ile Glu Gly Gln Ala Leu Gly Gln Lys Phe
65                  70                  75                  80

Ala Asp His Ala Lys His Phe Gly Ala Glu Phe His Tyr Ala Phe Ala
                85                  90                  95

Gln Lys Val Tyr Val Glu Gly Asp Tyr Lys Val Val Glu Leu Asp Asp
            100                 105                 110

Gly Asn Lys Val Lys Ala Lys Val Ile Leu Ala Thr Gly Thr Glu
        115                 120                 125

Pro Arg Lys Leu Gly Val Pro Gly Glu Ala Glu Phe Arg Gly Arg Gly
130                 135                 140

Val Thr Tyr Cys Ala Ala Cys Asp Gly Tyr Leu Phe Lys Asp Lys Asp
145                 150                 155                 160

Val Val Val Gly Gly Gly Asp Ser Ala Cys Asp Glu Ser His Phe
                165                 170                 175

Leu Ser Lys Ile Val Lys Ser Ile Thr Met Val Gln Asn Leu Pro Tyr
            180                 185                 190

Leu Thr Ala Ala Lys Val Leu Gln Glu Arg Val Leu Asn Asn Pro Lys
        195                 200                 205

Ile Lys Val Ile Thr Asn His Ile Val Lys Glu Ile Arg Gly Thr Ser
210                 215                 220

Lys Val Glu Glu Val Val Ile Val Asn Asn Asp Thr Lys Glu Glu Gln
225                 230                 235                 240

Val Ile Lys Ala Glu Gly Val Phe Ile Tyr Val Gly Leu Val Pro Gln
                245                 250                 255

Thr Gln Ile Phe Lys Gly Leu Val Asp Met Asn Asp Tyr Gly Tyr Ile
            260                 265                 270

Ile Thr Asp Glu Asn Met Glu Thr Asn Val Pro Gly Ile Tyr Ala Val
        275                 280                 285

Gly Asp Ile Arg Thr Lys Asn Leu Arg Gln Ile Val Thr Ala Ala Ala
290                 295                 300

Asp Gly Ala Ile Ala Val Glu His Ala Ala Lys Lys Tyr Phe
305                 310                 315

<210> SEQ ID NO 6
<211> LENGTH: 957
<212> TYPE: DNA
<213> ORGANISM: Artificial Sequence
<220> FEATURE:
<223> OTHER INFORMATION: nucleic acid sequences of Thioredoxin-disulfide reductase (CDR)

<400> SEQUENCE: 6

```
atgagcggat tgaattcga catgggaagc tttggtggaa atctaaagga atattacgac    60
atagctatca tcggtggtgg tccagcagga cttacggctg ctatttacgc aagaagggct   120
ggtttaacag ctctcgttat agaaaaggcc atcgaaggtg gtgcggttac tcaaacacat   180
gttgttgaaa actggcctgg tgagataagt attgaagggc aagctttagg acaaaaattc   240
gccgaccatg caaaacactt tggggctgaa ttccactatg cttttgcaca aaaagtgtat   300
gttgaaggtg attacaaagt tgttgaactt gacgacggaa taaagtaaa agccaaggtt   360 gtaattcttg ccactggtac agaaccaagg aaacttggcg tacctggcga agcagagttc   420
agaggtagag gagtcaccta ctgcgctgct tgtgatggtt atcttttcaa agataaggat   480
gtagtagttg taggtggcgg agatagcgct tgcgatgaat cgcacttcct ttcaaagatt   540
gttaaaagca tcaccatggt tcagaattta ccgtatttaa cagcggcgaa ggtcttacaa   600
gagagggtgc tcaataatcc aaaaattaag gttatcacaa atcacattgt gaaagagatt   660
agaggaacaa gcaaggttga agaggtcgtt atagtaaaca acgatacgaa agaagaacag   720
gttataaaag cagaaggtgt gttcatatac gttggattag ttccacaaac gcaaatattc   780
aaaggtcttg ttgatatgaa cgactacgga tacataatca ctgatgagaa tatggaaaca   840
aacgtaccag gaatctacgc agttggtgac atcaggacca agaatttgag acaaatagtc   900
accgcagctg cagacggtgc tatagccgtt gaacacgctg caaagaaata cttctaa     957
```

<210> SEQ ID NO 7
<211> LENGTH: 135
<212> TYPE: PRT
<213> ORGANISM: Artificial Sequence
<220> FEATURE:
<223> OTHER INFORMATION: amino acid sequences of Iron-sulfur assembly scaffold protein (SufE)

<400> SEQUENCE: 7

```
Met Ile Tyr Ser Glu Phe Ile Met Asp Tyr Ser Lys Leu Lys Lys Phe
1               5                   10                  15

His Gly Lys Ile Glu Asn Ala His Lys Val Glu Glu Gly Lys Asn Leu
            20                  25                  30

Ser Cys Gly Asp Glu Val Thr Leu Tyr Phe Leu Phe Asp Gly Asp Lys
        35                  40                  45

Ile Val Asp Val Lys Phe Glu Gly His Gly Cys Ala Ile Ser Gln Ala
    50                  55                  60

Ser Thr Asn Val Met Ile Glu Gln Ile Gly Lys Thr Lys Gln Glu
65                  70                  75                  80

Ala Leu Glu Met Met Lys Asn Ala Glu Asn Met Met Leu Gly Lys Glu
                85                  90                  95

Phe Asp Glu Asn Val Leu Gly Pro Ile Ile Asn Phe Tyr Asp Val Lys
            100                 105                 110

Asn Tyr Pro Met Arg Val Lys Cys Phe Leu Leu Pro Trp Lys Thr Leu
        115                 120                 125

Glu Ile Ala Leu Lys Asn Glu
    130                 135
```

<210> SEQ ID NO 8
<211> LENGTH: 408
<212> TYPE: DNA
<213> ORGANISM: Artificial Sequence
<220> FEATURE:
<223> OTHER INFORMATION: nucleic acid sequences of Iron-sulfur assembly scaffold protein (SufE)

<400> SEQUENCE: 8

```
atgatatact ctgaattcat aatggactat tcaaaactaa agaaatttca tggaaagata      60
gaaaacgctc acaaggtcga ggaaggtaaa aatctttcct gcggtgatga agtaacgctt     120
tattttcttt ttgatggcga caagatcgtc gatgtgaaat ttgaagggca cggttgtgcg     180
ataagtcagg catcaacaaa cgtgatgata gaacaaatca ttggaaaaac aaaacaagaa     240
gcacttgaaa tgatgaaaaa cgcagagaat atgatgcttg gaaaagaatt tgatgagaat     300
gttcttggac ctatcataaa tttttacgat gtgaagaatt atccaatgag ggttaaatgc     360
tttctacttc catggaaaac cctggagatt gctttaaaga atgaataa                 408
```

<210> SEQ ID NO 9
<211> LENGTH: 23
<212> TYPE: DNA
<213> ORGANISM: Artificial Sequence
<220> FEATURE:
<223> OTHER INFORMATION: F.aw1_cds_NdeI F

<400> SEQUENCE: 9

```
catatgcgct caacggtgtt ctc                                             23
```

<210> SEQ ID NO 10
<211> LENGTH: 23
<212> TYPE: DNA
<213> ORGANISM: Artificial Sequence
<220> FEATURE:
<223> OTHER INFORMATION: F.aw1_cds_XhoI R

<400> SEQUENCE: 10

```
ctcgagtcat tcgaaccacc tcc                                             23
```

<210> SEQ ID NO 11
<211> LENGTH: 32
<212> TYPE: DNA
<213> ORGANISM: Artificial Sequence
<220> FEATURE:
<223> OTHER INFORMATION: F.aw1_cbp_NdeI F

<400> SEQUENCE: 11

```
catatggaag aactaaaaag ctattacaaa cg                                   32
```

<210> SEQ ID NO 12
<211> LENGTH: 31
<212> TYPE: DNA
<213> ORGANISM: Artificial Sequence
<220> FEATURE:
<223> OTHER INFORMATION: F.aw1_cbp_XhoI R

<400> SEQUENCE: 12

```
ctcgagttaa agctctatct catacacttt g                                    31
```

<210> SEQ ID NO 13
<211> LENGTH: 25
<212> TYPE: DNA
<213> ORGANISM: Artificial Sequence
<220> FEATURE:
<223> OTHER INFORMATION: F.aw1_dsr_NdeI F

<400> SEQUENCE: 13

```
catatgagcg gatttgaatt cgaca                                           25
```

<210> SEQ ID NO 14

```
<211> LENGTH: 28
<212> TYPE: DNA
<213> ORGANISM: Artificial Sequence
<220> FEATURE:
<223> OTHER INFORMATION: F.aw1_dsr_XhoI R

<400> SEQUENCE: 14
ctcgagttag aagtatttct ttgcagcg                                              28

<210> SEQ ID NO 15
<211> LENGTH: 31
<212> TYPE: DNA
<213> ORGANISM: Artificial Sequence
<220> FEATURE:
<223> OTHER INFORMATION: F.aw1_sufE_NdeI F

<400> SEQUENCE: 15
gcgcatatga tatactctga attcataatg g                                          31

<210> SEQ ID NO 16
<211> LENGTH: 31
<212> TYPE: DNA
<213> ORGANISM: Artificial Sequence
<220> FEATURE:
<223> OTHER INFORMATION: F.aw1_sufE_XhoI R

<400> SEQUENCE: 16
ctcgagtaat tcattcttta aagcaatctc c                                          31
```